(12) United States Patent
Kannagi et al.

(10) Patent No.: US 7,601,348 B2
(45) Date of Patent: Oct. 13, 2009

(54) METHOD OF EXAMINING COLON CANCER AND COLON ADENOMA

(75) Inventors: Reiji Kannagi, Nagoya (JP); Mineko Izawa, Seto (JP); Takashi Muramatsu, Nagoya (JP); Kenji Uchimura, San Francisco, CA (US); Hideaki Hosokawa, Suita (JP)

(73) Assignees: Japan Science & Technology Agency, Saitama (JP); Local Government of Aichi Prefecture, Aichi-ken (JP); Wako Pure Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/568,544

(22) PCT Filed: Jul. 9, 2004

(86) PCT No.: PCT/JP2004/009805

§ 371 (c)(1),
(2), (4) Date: Sep. 22, 2006

(87) PCT Pub. No.: WO2005/019827

PCT Pub. Date: Mar. 3, 2005

(65) Prior Publication Data

US 2007/0196874 A1    Aug. 23, 2007

(30) Foreign Application Priority Data

Aug. 20, 2003    (JP)    ............... 2003-296216

(51) Int. Cl.
*A61K 39/395*    (2006.01)
(52) U.S. Cl. .................... 424/130.1; 435/7.23
(58) Field of Classification Search ........ None
See application file for complete search history.

(56) References Cited

U.S. PATENT DOCUMENTS

2002/0164748 A1    11/2002    Bistrup

FOREIGN PATENT DOCUMENTS

| JP | 06-000093 | 1/1994 |
| JP | 06-046878 | 2/1994 |
| JP | 11-313684 | 11/1999 |

OTHER PUBLICATIONS

Bruehl et al. (J. Biol. Chem. vol. 20, pp. 32642-32648, 2000) Abstract only.*
Streeter et al. (JCB, vol. 107, pp. 1853-1862, Nov. 1988).*
Hemmerich et al. (Immunity, vol. 15, pp. 237-247, Aug. 2001).*
Kenji Uchimura et al., "Specificities of N-Acetylglucosamine-6-O-sulfotransferases in Relation to L-section Ligand Synthesis and Tumor-associated Enzyme Expression", The Journal of Biological Chemistry, vol. 277, No. 6, Feb. 8, 2002, pp. 3979-3984.
Jiunn-Chern Yeh et al., "Novel Sulfated Lymphocyte Homing Receptors and Their Control by a Core1 Extension β1, 3-N-Acetylglucosaminyltransferase", Cell, vol. 105, Jun. 29, 2001, pp. 957-969.
Bruehl et al., "Minimal sulfated carbohydrates for recognition by L-selectin and the MECA-79 antibody," The Journal of Biological Chemistry, vol. 275, No. 42, pp. 32642-32648 (Oct. 20, 2000).
Izawa et al., "Expression of sialyl 6-sulfo Lewis X is inversely correlated with conventional sialyl Lewis X expression in human colorectal cancer," Cancer Research, vol. 60, No. 5, pp. 1410-1416 (Mar. 1, 2000).
Jin Kyu Lee et al., "Cloning and characterization of a mammalian N-acetylglucosamine-6-sulfotransferase that is highly restricted to intestinal tissue," Biochemical and Biophysical Research Communications, vol. 2, No. 263, pp. 543-549 (Sep. 1999).
Kimura et al., "Reconstitution of functional L-selectin ligands on a cultured human endothelial cell line by cotransfection of α-1→3 fucosyltransferase VII and newly cloned GlcNAcβ:6-sulfotransferase cDNA," Proceedings of the National Academy of Sciences of USA, vol. 96, pp. 4530-4535 (Apr. 1999).

(Continued)

*Primary Examiner*—Larry R. Helms
*Assistant Examiner*—Meera Natarajan
(74) *Attorney, Agent, or Firm*—Jenkins, Wilson, Taylor & Hunt, P.A.

(57) ABSTRACT

The present invention provides a method for examining colorectal cancer and colorectal adenoma, which enables to detect colorectal cancer patients and patients at high risk of colorectal cancer at a high probability and is useful for diagnosis of colorectal cancer and colorectal adenoma, and provides the examination reagents thereof. The present inventors discovered that there are significant differences in the distribution of GlcNAc-6-sulfotransferase isozymes, sulfation enzymes of sugar residues, among non-cancer colorectal tissues, colorectal cancer tissues and colorectal adenoma tissues. Furthermore the inventors applied the discovery to diagnosis and found that colorectal cancers and adenomas are detected specifically by assaying a definite range of GlcNAc-6-sulfated sugar residues in tissues from patients or feces samples. MECA-79 antibody (Pharmingen, catalog No. 09961D, Distributor: Becton Dickinson), reacting with GlcNAc-6-sulfated sugar residues, which are produced specifically by the enzyme present in colorectal cancer and colorectal adenoma tissues could be used for the examination of colorectal cancers and colorectal adenomas.

10 Claims, 6 Drawing Sheets

OTHER PUBLICATIONS

Seko et al., "Biochemical differences between two types of N-acetylglucosamine:→6sulfotransferases in human colonic adenocarcinomas and the adjacent normal mucosa: specific expression of a GlcNAc:→6sulfotransferase in mucinous adenocarcinoma," Glycobiology, vol. 10, No. 9, pp. 919-929 (Sep. 2000).

Seko et al., "Ectopic expression of a GlcNAc 6-O-sulfotransferase, GlcNAc6ST-2, in colonic mucinous adenocarcinoma," Glycobiology, IRL Press, GB, vol. 12, No. 6, pp. 379-388 (2002).

Streeter et al., "Immunohistologic and functional characterization of a vascular addressin involved in lymphocyte homing into peripheral lymph nodes," The Journal of Cell Biology, vol. 107, No. 5, pp. 1853-1862 (Nov. 1988).

Supplementary European Search Report for European Patent Application No. 04747273.3-1223 PCT/JP2004009805 dated Apr. 18, 2008.

Uchimura et al., "Specificities of N-acetylglucosamine-6-O-sulfotransferases in relation to L-selectin ligand synthesis and tumor-associated enzyme expression," Journal of Biological Chemistry, vol. 277, No. 6, pp. 3979-3984 (Feb. 8, 2002).

Akira Seko et al., "Ectopic Expression of A GlcNAc 6-O-Sulfotransferase, GlcNAc6ST-2, in Colonic Mucinous Adenocarcinoma", Glycobiology, vol. 12, No. 6, 2002, pp. 379-388.

* cited by examiner

GlcNAc6ST-1
Transduced cells

HEC-GlcNAc6ST
Transduced cells

I-GlcNAc6ST
Transduced cells

← Colorectal Cancers (8 cases)

← Colorectal Adenomas (8 cases)

← Benign Colorectal Disorders (8 cases)

← Normal Healthy Subjects (8 cases)

Figure 6

BD PharMingen Technical Data Sheet

Page 1 of 2

PURIFIED RAT ANTI-MOUSE PNAd CARBOHYDRATE EPITOPE (CD62L Ligand) MONOCLONAL ANTIBODY

PRODUCT INFORMATION

| | |
|---|---|
| Catalog Number: | 553863 (Was: 09961D), 0.5 mg |
| Description: | Purified anti-mouse PNAd Carbohydrate Epitope (CD62L Ligand) |
| Clone: | MECA-79 |
| Immunogen: | Collagenase-dispersed BALB/c lymph node stroma[1] |
| Isotype: | Rat (Wistar) IgM, κ |
| Contents: | Purified immunoglobulin in 10 mM phosphate buffer, pH 7.2 with 500 mM NaCl and 0.09% (w/v) sodium azide. |

SPECIFICITY

The MECA-79 antibody reacts with sulfate-dependent carbohydrate epitopes of peripheral lymph node addressin (PNAd).[2] The MECA-79-reactive antigen is closely associated with the carbohydrate ligands for L-selectin (e.g., CD34, GlyCAM-1, MAdCAM-1), which are expressed on high endothelial venules (HEV) in lymphoid tissues and at sites of chronic inflammation.[1,2,3,4,5,6] Cross-reactivity with human,[3,4] ovine,[7] bovine,[7] primate,[7] and porcine[8] tissues has been observed. MECA-79 antibody inhibits L-selectin- dependent lymphocyte and platelet homing to lymph nodes in vivo[1,9] and in vitro adhesion to lymphoid tissue HEV[1,4] and immobilized PNAd.[3,9,10]

PREPARATION AND STORAGE

The antibody was purified from tissue culture supernatant by affinity chromatography. The antibody solution should be stored undiluted at 4°C.

USAGE

This antibody has been tested by immunohistochemical staining (IHC) of citrate-pretreated formalin-fixed paraffin-embedded sections (5 - 20 µg/ml) to assure specificity and reactivity. Other reported applications include IHC of acetone-fixed frozen sections,[1,4,5] immunoprecipitation[2,3] western blot analysis,[10] and in vitro and in vivo adhesion blocking.[1,3,4,9,10] Since applications vary, each investigator must determine dilutions appropriate for individual use.

Caution: Sodium azide is a reversible inhibitor of oxidative metabolism; therefore, antibody preparations containing this preservative agent must not be used in cell cultures nor injected into animals. Sodium azide may be removed by washing stained cells or plate-bound antibody or dialyzing soluble antibody in sodium azide-free buffer. Since endotoxin may also affect the results of functional studies, we recommend the NA/LE™ (No Azide/Low Endotoxin) antibody format for in vitro and in vivo use.

REFERENCES

1. Streeter, P.R., B.T.N. Rouse, and E.C. Butcher. 1988. Immunohistologic and functional characterization of a vascular addressin involved in lymphocyte homing into peripheral lymph nodes. J. Cell Biol. 107: 1853 - 1862.
2. Hemmerich, S, E.C. Butcher, and S.D. Rosen. 1994. Sulfation-dependent recognition of high endothelial venules (HEV)-ligands by L-selectin and MECA 79, an adhesion-blocking monoclonal antibody. J. Exp. Med. 180: 2219 - 2226.
3. Berg, E.L., M.K. Robinson, R.A. Warnock, and E.C. Butcher. 1991. The human peripheral lymph node vascular addressin is a ligand for LECAM-1, the peripheral lymph node homing receptor. J. Cell Biol. 114: 343 - 349.
4. Michie, S.A., P.R. Streeter, P.A. Bolt, E.C. Butcher, and L.J. Picker. 1993. The human peripheral lymph node vascular addressin. An inducible endothelial antigen involved in lymphocyte homing. Am. J. Pathol. 143: 1688 - 1698.
5. Faveeuw, C., M.-C. Gagnerault, and F. Lepault. 1994. Expression of homing and adhesion molecules in infiltrated Islets of Langerhans and salivary glands of nonobese diabetic mice. J. Immunol. 152: 5969 - 5978.

Please see Page 2.

Figure 7

REFERENCES (Continued)

6. Maly, P., A.D. Thall, B. Petryniak, C.E. Rogers, P.L. Smith, R.M. Marks, R.J. Kelly, K.M. Gersten, G. Cheng, T.L. Saunders, S.A. Camper, R.T. Camphausen, F.X. Sullivan, Y. Isogai, O. Hindsgaul, U.H. von Andrian, and J.B. Lowe. 1996. The α(1,3)fucosyltransferase Fuc-TVII controls leukocyte trafficking through an essential role in L-, E-, and P-selectin ligand biosynthesis. *Cell* 86: 643 - 653.
7. Butcher, E.C. Personal communication.
8. Binns, R.M., A. Whyte, S.T. Licence, A.A. Harrison, Y.T.M. Tsang, D.O. Haskard, and M.K. Robinson. 1996. The role of E-selectin in lymphocyte and polymorphonuclear cell recruitment into cutaneous delayed hypersensitivity reactions in sensitized pigs. *J. Immunol.* 157: 4094 - 4099.
9. Diacovo, T.G., K.D. Puri, R.A. Warnock, T.A. Springer, and U.H. von Andrian. 1996. Platelet-mediated lymphocyte delivery to high endothelial venules. *Science* 273: 252 - 255.
10. Puri, K.D., E.B. Finger, G. Gaudernack, and T.A. Springer. 1995. Sialomucin CD34 is the major L-selectin ligand in human tonsil high endothelial venules. *J. Cell Biol.* 131: 261 - 270.

For Research Use Only. Not For Diagnostic or Therapeutic Use.

Conditions: BD PharMingen will not be responsible for violations or patent infringements which may occur with the use of our products.

Hazardous Ingredient: Sodium Azide. Avoid exposure to skin and eyes, ingestion, and contact with heat, acids, and metals. Wash exposed skin with soap and water. Flush eyes with water. Dilute with running water before discharge into plumbing.

METHOD OF EXAMINING COLON CANCER AND COLON ADENOMA

FIELD OF THE INVENTION

The present invention relates to a method for examining human colorectal cancers and colorectal adenomas, and to antibodies and examination reagents thereof.

PRIOR ART

Since the number of colorectal cancer patients is increasing year by year, a method for early detection is necessary. Although, immunological fecal occult blood test and various tumor markers are used at present for the examination of colorectal cancers, these methods do not have satisfactory positive rates. Namely, the positive rate of immunological fecal occult blood test used for the examination of colorectal cancers is 50-60%. As to the tumor markers of colorectal cancers, carcino-embryonic antigen (CEA), CA19-9, STX, which are used for examining the therapeutic effect and for monitoring recurrence, are not satisfactory as tumor markers for early detection of colorectal cancers.

The colon is divided into right-half and left-half drawing a line at the flexure coli and colorectal cancers in right-half result frequently in pseudo-positive by fecal occult blood test using an anti-hemoglobin antibody, which is pervasively used for the detection of colorectal cancers. Therefore, development of a test method contributing to increased early diagnosis rate particularly of the right-half colorectal cancers is expecting. As to the laboratory diagnosis of colorectal adenomas, which is regarded as the birthplace of colorectal cancers, suitable methods of detecting are not available and people rely inevitably on endoscopy at the present time. Simple method of diagnosing colorectal adenomas will be beneficial to classify patients into groups necessary and unnecessary for endoscopy, and contribute to early detection of colorectal cancers.

Although the sulfation of sugar residues is active in a normal large bowel, it is known to be remarkably reduced in colorectal cancers. Namely, both 3'-sulfation of galactose and 6-sulfation of N-acetylglucosamine (hereinafter referred to as [GlcNAc]), which are abundant in colorectum, are reduced (reference 1). A number of GlcNAc-6-sulfotransferase isozymes have been known in colorectal cancer tissues and in non-cancer colorectal tissues of patients, and I-GlcNAc6ST is significantly decreased in course of carcinogenesis, which leads to the reduced sulfation of sugar residues in colorectal cancer (reference 2). While, GlcNAc6ST-1, one of the isozymes in a normal colorectum, does not show significant changes in the level in course of carcinogenesis. Furthermore, HEC-GlcNAc6ST, another isozyme, increases significantly in colorectal cancer (reference 3).

HEC-GlcNAc6ST, which increases in colorectal cancers, synthesizes 6-sulfated GlcNAc and carries out sulfation of GlcNAc in various sugar residues. Therefore, there are a huge variety of the structures of intra-cellularly synthesized sugar residues and their antigenicity. Since GlcNAc6ST-1 and I-GlcNAc6ST also synthesize 6-sulfatedGlcNAc, only the fact that 6-sulfatedGlcNAc is synthesized from HEC-GlcNAc6ST cannot be used as a specific method for diagnosis of colorectal cancer. However, it is known that the substrate selectivity of GlcNAc6ST-1 and I-GlcNAc6ST is more specific than that of HEC-GlcNAc6ST (reference 3, 4). Therefore, certain 6-sulfated sugar residues might be produced by HEC-GlcNAc6ST, but not by GlcNAc6ST nor by I-GlcNAc6ST. However, an actual system for diagnosis of colorectal cancers has not been established.

On the other hand, the monoclonal antibody (MECA-79 antibody, reference 5), commercially available as an antibody against an immunological homing receptor of lymphocytes, is known to react with chemically synthesized GlcNAc6-sulfated sugar residues (reference 7). Moreover, the antigens recognizable by the antibody (MECA-79) are reported to emerge on the cell surface, when a mouse gene encoding HEC-GlcNAc6ST enzyme is transduced into CHO cells (hamster ovary cells) (reference 7). However, it has not been known whether the antigens are recognizable by MECA-79 antibody emerged on human cancer cells.

reference 1: Izawa, M. et al., Cancer Res., 60: 1410-1416, 2000.
reference 2: Abstract of the 22nd Research Meeting of Japan Molecular Tumor Maker pp42-43, 2002.
reference 3: Seko, A. et al., Glycobiology, 10:919-929, 2000
reference 4: Seko, A. et al., Glycobiology, 12:379-388, 2002
reference 5: Streeter, P. R. et al., J. Cell Biol. 107: 1853-1862, 1988.
reference 6: Bruehl, R. E. et al., J. Biol. Chem. 275: 32642-32648, 2000
reference 7: Yeh, J. C. et al., Cell 105: 957-969, 2001.

PROBLEMS TO BE SOLVED BY THE INVENTION

The present invention provides a method for examining colorectal cancer and colorectal adenoma, which enables to detect colorectal cancer patients and patients at high risk of colorectal cancer at a high probability and is useful for diagnosis of colorectal cancer and adenoma, and provides the examination reagents thereof.

MEANS TO SOLVE THE PROBLEMS

The present inventors discovered that there are significant differences in the distribution of GlcNAc-6-sulfotransferase isozymes, sulfation enzymes of sugar residues, between non-cancer colorectal tissues and colorectal cancer tissues or colorectal adenoma tissues, as a result of investigations. Then the inventors found that colorectal cancers and adenomas could be detected specifically by assaying 6-sulfated sugar residues, which are synthesized only by HEC-GlcNAc6ST, but not by GlcNAc6ST-1 nor by I-GlcNAc6ST, in tissues of patients and in fecal samples. Previously, many antibodies such as AG223 (Biochem. (Tokyo), 124:670-678, 1998), G152, G72, AG97, AG107, AG273, G2706, G27011, G27039 (all above, J. Biol. Chem., 273:11225-11233, 1998) are known as those reacting with GlcNAc-6-sulfated sugar residues. Meanwhile, MECA-79 antibody (Pharmingen, catalog No. 09961D, distributor: Becton Dickinson), which is commercially available as immunological homing receptor of lymphocytes, is known to react in some way with GlcNAc-6-sulfated sugar residues (reference 6).

The inventors made a search for an antibody, which have little reactivity to such cells as normal colorectal epithelial cells expressing GlcNAc-6-sulfated sugar residues, but have strong reactivity to cells with such GlcNAc-6-sulfated sugar residues as expressed in cancer cells, by screenings these antibodies. Then the obtained antibodies were assayed against samples from patients and were shown to be highly positive to colorectal cancer cells. The above results lead to completion of the present invention.

In other words, the present invention is a method for examining colorectal cancer and colorectal adenoma comprising assaying the reactivity of an antibody to tissues, body fluid or feces of patients, or extracts thereof, wherein said antibodies react with such antigen that is present in cells expressing HEC-GlcNAc6ST gene encoding GlcNAc-6-sulfotransferase and that is absent or almost absent in cells expressing GlcNAc6ST-1 or I-GlcNAc6ST gene. The antigen may be present in cells transduced with HEC-GlcNAc6ST gene and is absent or almost absent in cells transduced with GlcNAc6ST-1 gene or I-GlcNAc6ST gene.

The antigen may be represented by the formula below:

R1-Gal β1-3/4(SO$_3$-6) GlcNAcβ1-R2 where, R1 represents sugar residues added by other enzymes and is not limited in structure. Gal β represents β galactose, GlcNAc β represents β N-acetylglucosamine, Gal β1-3/4 represents binding of 1 position of Gal β and 3 position and/or 4 position of GlcNAc β, (SO$_3$-6) represents addition of a sulfate group to 6 position of GlcNAc β, R2 represents –3GalNAc α, –3Gal β or –2Manα and binds to 1 position of GlcNAc β. As the antibody, MECA-79 antibody (Pharmingen, catalog No. 09961D, shown in FIGS. 6 and 7) is preferably used.

Also, the present invention is a method for examining colorectal cancer and colorectal adenoma, which comprises reactivity of MECA-79 antibody or its equivalent with tissues, body fluid, feces or extracts thereof of examination subjects.

Furthermore, the present invention is any of said methods comprising the reaction of a labeled probe to said antibody and qualitative or quantitative assay of the label. The preferable method for examination comprises fixing the antigens present in tissues, body fluid or feces or extracts thereof of patients to a membrane, reacting with the antibody, reacting with a labeled probe and detecting the label. It is preferable to insert washing procedures appropriately between the above processes. Said probe includes anti-human-IgG, antibody, protein G, protein A, and protein L. These probes are usually labeled. Said labels include a radioactive isotope (125I) and enzymes (peroxidase, alkaline phosphatase). An antibody with enzyme may involve observation of a change (i.e. color change) by the reaction between the enzyme and the substrate.

Moreover, the present invention is an antibody reacting specifically with an antigen carrying sugar residues, which are present in cells expressing HEC-GlcNAc6ST gene encoding GlcNAc-6-sulfotransferase and are absent or almost absent in cells expressing GlcNAc6ST-1 or GlcNAc6ST gene (excluding MECA-79 antibody). Still furthermore, the present invention is an antibody reacting specifically with an antigen carrying sugar residues, which are present in cells transduced with HEC-GlcNAc6ST gene encoding GlcNAc-6-sulfotransferase and are absent or almost absent in cells transduced with GlcNAc6ST-1 or GlcNAc6ST gene (excluding MECA-79 antibody).

Still moreover, the present invention is an antibody (excluding MECA-79 antibody) reacting specifically with an antigen carrying sugar residues, which are present in tissues, body fluid or feces of patients with colorectal cancers and colorectal adenomas and expressed by the following general formula:

R1-Gal β1-3/4(SO$_3$-6) GlcNAcβ1-R2

(in the formula, each note is the same to the above).

Also, the present invention is an examination reagent of colorectal cancer and colorectal adenoma comprising any of these antibodies, including MECA-79 antibody, as a main component.

BRIEF DESCRIPTION OF THE DRAWINGS

FIG. 6 shows a catalog of MECA-79 antibody (Pharmingen, catalog No. 09961D).

FIG. 7 shows a catalog of MECA-79 antibody (Pharmingen, catalog No. 09961D).

DETAILED DESCRIPTION OF THE INVENTION

Figure 1:
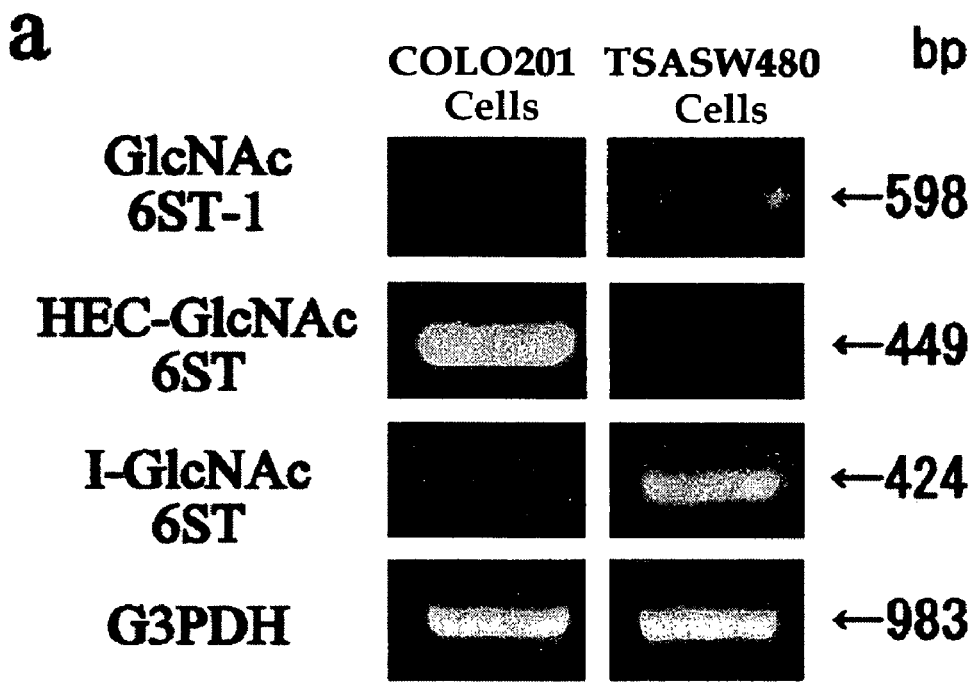
FIG. 1 shows the results of flowcytometric analysis using MECA-79 antibody on colorectal cancer cells (COLO201 cells) and on normal colorectal epithelial cells (SW480 cells treated with Tricostatine A). a shows the enzyme specificity of colorectal cancer cells (COLO201 cells) and normal colorectal epithelial cells (SW480 cells). b shows the results of flowcytometric analysis on the reactivity of anti-6-sulfated sugar residues antibody with the above 2 kinds of cells. The ordinate shows the cell frequency (the number of cells) and the abscissa axis shows the fluorescence (Arbitrary Unit).
Figure 1:
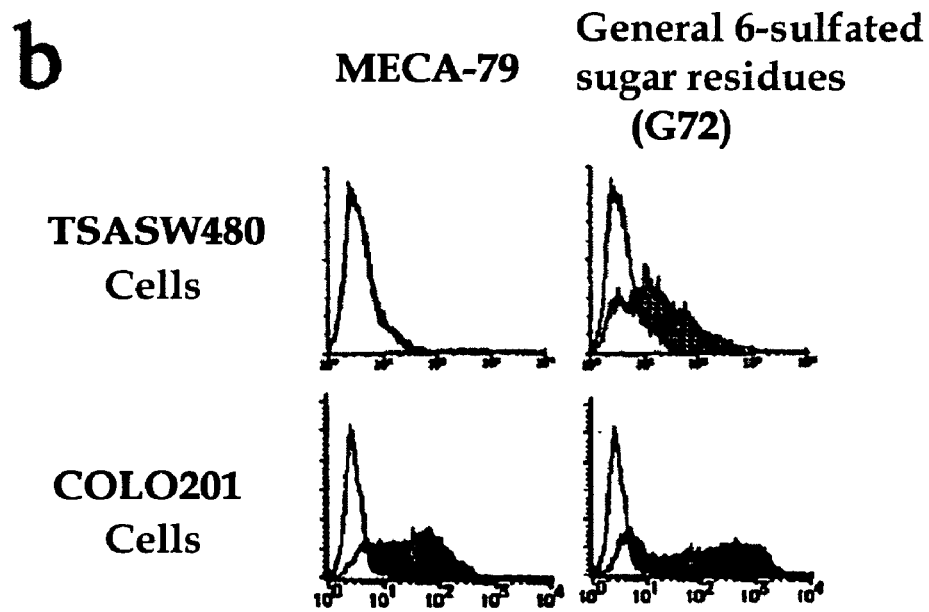

The structure of 6-sulfated sugar residues, which are little synthesized by GlcNAc6ST-1 or by I-GlcNAc6ST, but are synthesized only by HEC-GlcNAc6ST is expressed as the following general formula:

R1-Galβ1-3/4(SO$_3$-6) GlcNAcβ1-R2.

GlcNAcβ, which is the substrate of GlcNAc6-sulfotransferase in a body, is carried by various sugar residue carrier. R2 shows the carrier.

HEC-GlcNAc6ST has been known to transfer sulfate residues to all kinds of GlcNAcβ1-R2 previously tested according to our research and other people's research (references 4 and 7). In contrast, GlcNAc6ST-1 and I-GlcNAc6ST transfer sulfate residues only to such GlcNAcβ-R2 as accompanied with a specific form of R2. The case, which HEC-GlcNAc6ST but not GlcNAc6ST-1 nor I-GlcNAc6ST can transfer sulfate residues, is known as a case when R2 is –3GalNAcα (the structure after sulfation is SO$_3$-6GlcNAcβ1-3GalNAcα), a case when R2 is –3Galβ (the structure after sulfation is SO$_3$-6GlcNAcβ1-3Galβ) and a case when R2 is –2Manα (the structure after sulfation is SO$_3$-6GlcNAcβ1-2Manα)(J. Biol. Chem., 277: 3979-3984, 2002 and Glycobiology, 12: 379-388, 2002). In the examination method of the present invention, a specific antibodies to any of the three cases and antibodies cross reacting to all three sugar residues may be usable.

GlcNAc-6-sulfotransferase adds sulfate group to distal GlcNAc of sugar residues and synthesizes 6-sulfated GlcNAc (i.e. $SO_3$-6GlcNAc) intra-cellularly. However, after synthesis of distal 6-sulfated GlcNAc of sugar residues, the modified sugar residues are further added sugar residues (R1) by other enzyme groups intra-cellularly, and a large variety of the structure and antigenicity of the sugar residues are finally synthesized and produced from cells. Generally the structure added to 6-sulfated GlcNAc is Galβ1-4 and Galβ1-3 (referred to as Galβ1-3/4). Moreover, it is known that NeuAc α2-3/6, $SO_3$-3/6, and Fuc α1-2/3/4 are added to the 6-sulfated GlcNAc. The R1 part is added after the synthesis of 6-sulfated GlcNAc by GlcNAc-6-sulfotransferase. Therefore, R1 part is not related to the substrate specificity of such GlcNAc-6-sulfotransferases as HEC-GlcNAc6ST, GlcNAc6ST-1 and I-GlcNAc6ST.

The antigens with the above sugar residues are present in cancer tissues obtained from colorectal cancer patients by biopsy or by surgical operation, and present in such samples as serum, ascites and feces containing the antigens. Also, the antigen may be easily extracted from these samples using phosphate buffered saline. Also, the antibody against this sugar residue antigen could be obtained by known arts producing antibodies (e.g. Methods in Enzymology, 312: 160-179, 2000; Methods in Molecular Biology, 199: 203-218, 2002 et al.).

The GlcNAc-6-sulfated sugar residues detected by the present invention are positive not only in colorectal cancers but also in colorectal adenomas, which are regarded as the birthplace of colorectal cancers. Therefore, using the sugar residues as a target of screening test, a group of patients with colorectal adenomas, for whom endoscopic examination or follow-up is required, could be detected. Compared with the occult blood test with anti-hemoglobin antibody, which is currently used for screening of colorectal cancers, the present method has higher yield of detection of colorectal adenomas. Also, 6-sulfated sugar residues are originally abundant in right-half of colorectum, if a colorectum is separated in right-half and left-half, therefore the above method of diagnosis is particularly useful for the diagnosis of colorectal cancers and colorectal adenomas generated in right-half colorectum. Since colorectal cancers in right-half are not frequently positive by fecal occult blood test using anti-hemoglobin antibody, concomitant use of the present method may contribute to increased yield of positive diagnosis in right-half colorectal cancers.

The following examples are provided to illustrate the present invention, but are not intended to limit the scope thereof.

EXAMPLE 1

Gene expression of GlcNAc-6-sulfotransferase isozymes was examined by RT-PCR on human-derived colorectal cancer cells and on normal colorectal epithelial cells. In the RT-PCR analysis, PCR primers for detection of the expression of HEC-GlcNAc6ST gene (Genebank, AF131235) are synthetic oligonucleotides of SEQ ID NO. 1 for upper strand side and those of SEQ ID NO. 2 for lower strand side (Tm=59° C.), those for GlcNAc6ST-1 gene (Genebank, AB011451) are synthetic oligonucleotides of SEQ ID NO. 3 for upper strand side and those of SEQ ID NO. 4 for lower strand side (Tm=62° C.) and those for I-GlcNAc6ST gene (Genebank, AF176838) are synthetic oligonucleotides of SEQ ID NO. 5 for upper strand side and those of SEQ ID NO. 6 for lower strand side (Tm=60° C.).

The results are shown in FIG. 1a. COLO201 cells are typical cells showing colorectal cancer pattern, which expresses strongly HEC-GlcNAc6ST gene and little GlcNAc6ST-1 and I-GlcNAc6ST genes. TSA-SW480 cells treated SW480 cells with tricostatinA are typical cells showing normal epithelial pattern, which little expresses HEC-GlcNAc6ST gene, but significantly expresses GlcNAc6ST and I-GlcNAc6ST genes.

Then, a number of anti6-sulfated sugar residues antibody were screened based on the reactivity to the above two kinds of cells. In other words, antibodies, which react well with COLO201 cells and not react with TSA-SW480 cells, were searched. The screening of the reactivity between cells and antibodies was performed by flowcytometric analysis by use of FACScan (Becton Dickinson) stained cells with indirect fluorescent antibody method (the first antibody 1.0 µg/ml, 4° C., 30 min, the second antibody rabbit anti-rat IgM antibody (Zymed Laboratories), 4° C., 30 min). A typical result of the analysis is shown in FIG. 1b. MECA-79 antibody (Pharmingen, catalog No. 09961D, Distributor: Becton Dickinson) showed strong reactivity with COLO201 cells, but showed little reactivity with TSA-SW480 cells. The above result showed that MECA-79 antibody is a preferable antibody for diagnosis of colorectal cancers. While, G72 antibody used as a control (J. Biol. Chem., 273: 11225-11233, 1998) reacted significantly with both COLO201 cells and TSA-SW480 cells and is not appropriate for diagnosis of colorectal cancers.

EXAMPLE 2

In this example, cells transduced with HEC-GlcNAc6ST gene, GlcNAc6ST-1 gene or I-GlcNAc6ST gene were prepared. Then flowcytometric analysis for these cells was performed using MECA-79 antibody.

For the preparation of cells transduced with HEC-GlcNAc6ST gene, the gene (Genebank, AF131235) inserted into pcDNA3.1 vector was used. For those with GlcNAc6ST-1 gene, the gene (Genebank, AB011451) inserted into pIRES1hygro vector was used. For those with I-GlcNAc6ST gene, the gene (Genebank, AF176838) inserted into pCDNA3.1 vector was used. The flowcytometric analysis was performed as in Example 1.

Figure 2:
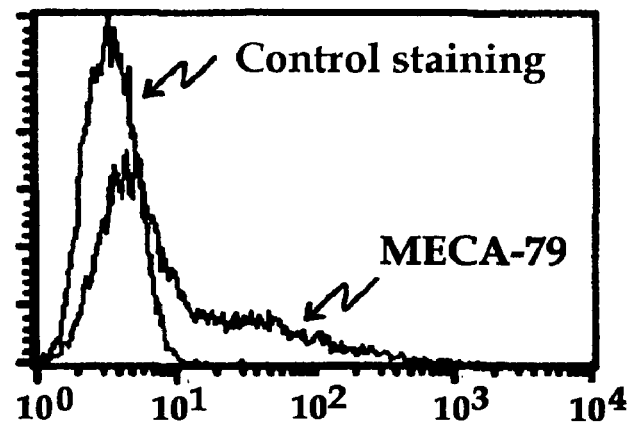
FIG. 2 shows the result of the flowcytometric analysis on the reactivity of MECA-79 antibody with cells transduced with HEC-GlcNAc6ST gene, GlcNAc6ST-1 gene or I-GlcNAc6ST gene. The ordinate shows the cell frequency (the number of cells) and the abscissa axis shows the fluorescence (Arbitrary Unit).
Figure 2:
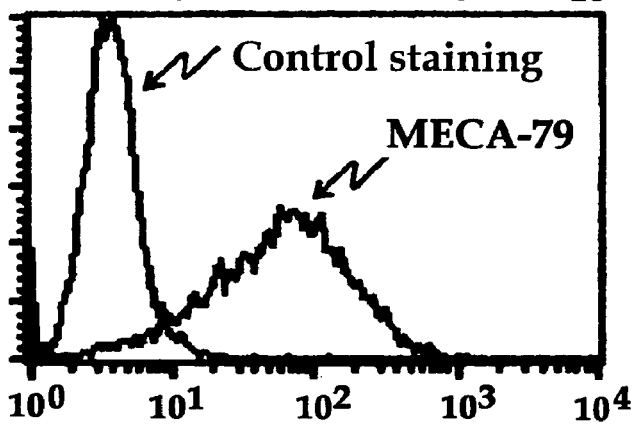
Figure 2:
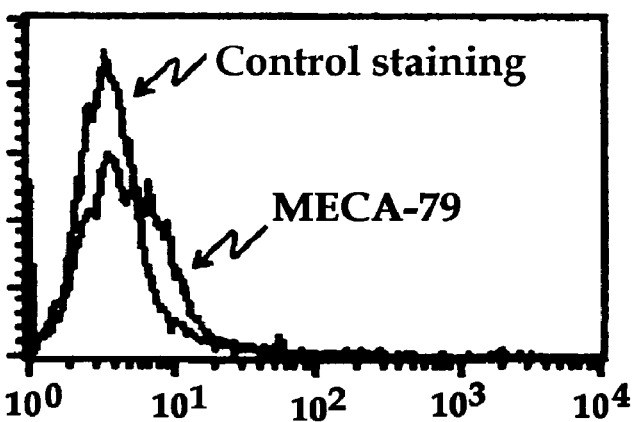

The results are shown in FIG. 2. MECA-79 antibody reacted strongly with those cells transduced with HEC-GlcNAc6ST, but reacted with slightly those cells transduced with GlcNAc6ST gene or I-GlcNAc6ST gene.

EXAMPLE 3

Colorectal cancer tissues derived from patients (31 cases) were stained with immunohistological staining using MECA-79 antibody. For immunohistological staining, frozen sections with 10 µm thick were used, 1.0 µg/ml MECA-79 antibody was used as the first antibody, and a reagent kit (Vectastain) of Vecta Co. containing anti-rat IgM antibody was used as the second antibody according to the protocol of the company.

Figure 3:
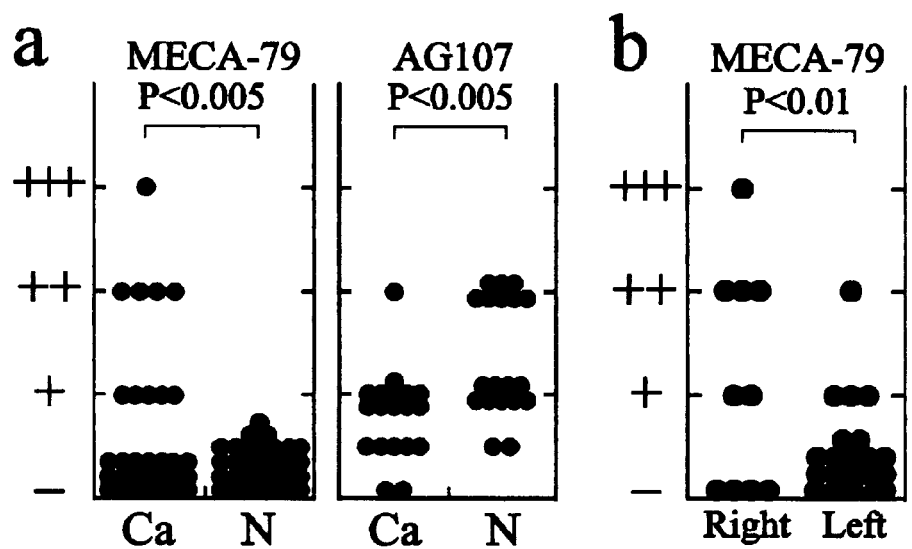
FIG. 3 shows the photographs of tissues stained with MECA-79 antibody of a colorectal cancer patient. Ca shows a colorectal cancer tissue and N shows non-cancer colorectum tissue.

The results are shown in FIG. 3. The antibody does not react with non-cancer colorectal mucosa (N) (0 case/31 ca31 cases, 32%). Positive reaction rate is higher for cancers in right-half colorectum (60%) and lower for those in left-half colon (19%).

Figure 4:
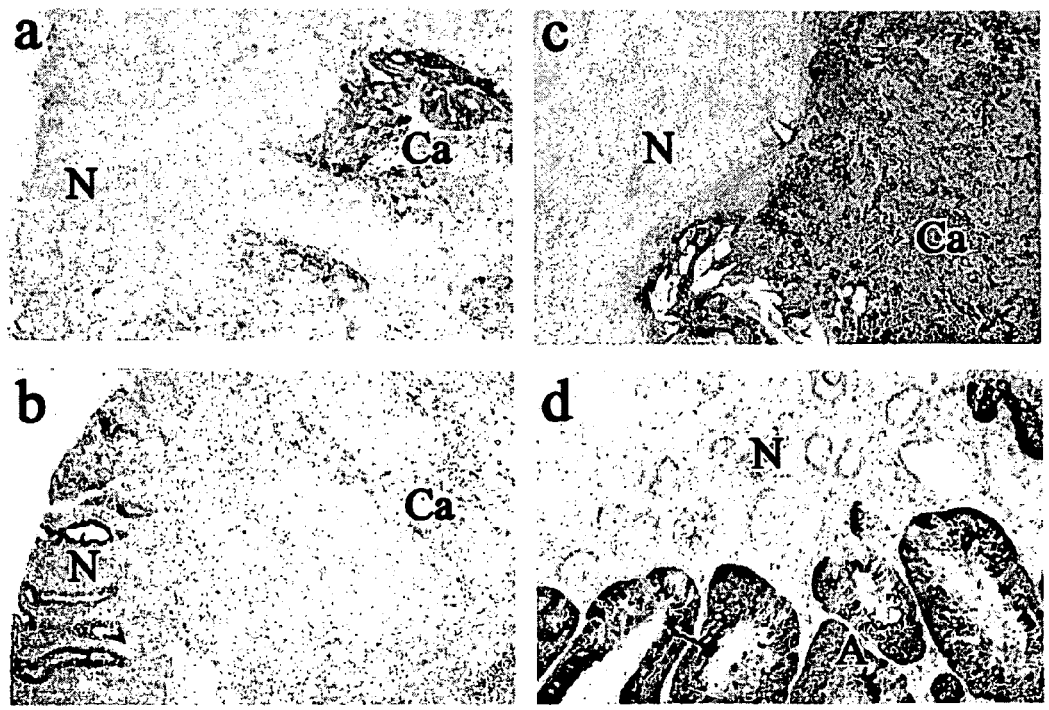
FIG. 4 shows the photographs of tissues of colorectal cancer and normal colorectum of a patient stained with MECA-79 antibody. Ca shows cancer tissues and N shows non-cancer colorectum tissues in a to c. N shows a non-adenoamotous colorectum tissue and A shows adenomatous cells in d. The black part (brown in color) shows the presence of antigens recognizable by the antibody and the gray part (faint blue in color) shows control staining with methylene blue.

A typical stained photographs are shown in FIG. 4.

FIG. 4a shows the stained photograph of a colorectal cancer tissue (ca) and a colorectal non-cancer tissue (N) of a patient. The colorectal cancer tissue is strongly stained but the non-cancer tissue is little stained.

FIG. 4b shows the photograph of the same tissue stained using AG107 antibody. Since AG107 antibody reacts with general GlcNAc-6-sulfated sugar residues, the non-cancer tissue (N) was stained well much more than the cancer tissue (Ca) in contrast to 4a and GlcNAc-6-sulfated sugar residues only could not be used for the specific detection of cancer tissues. Namely, use of such antibody as MECA-79, which detects the specific GlcNAc-6-sulfated sugar residues abundant in colorectal cancers and colorectal adenomas, could be applied for the specific detection.

FIG. 4c shows the example of the expression of the sugar residues in a colorectal cancer tissue derived from right-half colorectum. That the cancer tissue is strongly stained shows strong expression of the sugar residues.

FIG. 4d shows the expression in an adenomatous polyposis coli. N shows non-adenomatous colorectal tissue and A shows adenomatous cells. The adenomatous part of A is well stained by MECA-79 antibody. GlcNAc-6-sulfated sugar residues, which could be detected by MECA-79 antibody, are expressed abundantly in non-cancer adenomatous polyposis as well as in cancer tissues. Adenomatous polyposis coli, which is benign by itself but is regarded as the birthplace of colorectal cancer, could be detected credibly.

EXAMPLE 4

In this example, an enzyme-linked immunosorbent assay, which is a simple qualitative test and uses MECA-79 antibody for the reaction with fecal extracts of colorectal cancer patient, confirmed the emergence of GlcNAc-6-sulfated sugar residues in feces of patients. Sometimes sugar residue antigens are decomposed by enzymes secreted from fecal bacterium and could not be detected in feces. Therefore, the confirmation is important for the practicability of the present invention.

0.1 g human feces was dispersed in 1 ml fecal extraction buffer (10 mM PBS, 1% BSA, pH 7.5), centrifuged at 8,000 g for 15 min at 4° C., and the supernatant was recovered. To 40 μl supernatant, 120 μl extraction buffer was added and the sample was prepared. The sample was blotted to a PVDF membrane (Immobilon, Milipor, Lot K2JN2659B) by suction and the membrane was reacted with MECA-79 antibody, rabbit anti-rat IgM antibody, POD labeled goat anti-rabbit IgG antibody, and avidin-biotin complex solution, sequentially, after blocked for nonspecific reactions, and stained in NTB solution.

Figure 5:
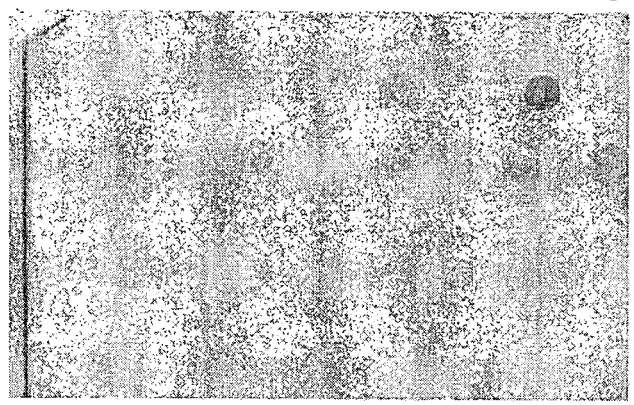
FIG. 5 shows the reactivity of MECA-79 antibody with fecal extracts of patients. Each row from above shows colorectal cancer 8 cases, colorectal adenoma 8 cases, benign 8 cases and healthy control 8 cases, respectively.

The results are shown in FIG. 5.

Positive results are 4 cases in 8 cases of colorectal cancers (50%) and 4 cases in 8 cases of colorectal adenomas (50%). For benign disorders cases, 1 case gives a slight positive result and almost all cases of normal healthy subjects are negative.

What is claimed is:

1. A method for examining colorectal cancer and colorectal adenoma comprising:
    a) providing a patient in need of screening for colorectal cancer or adenoma; and
    b) assaying the binding of an antibody to an antigen in tissues, body fluid or feces, or extracts thereof, of the patient wherein said antigen is present in cells expressing HEC-GlcNAc6ST gene encoding GlcNAc-6-sulfotransferase and is absent in cells expressing GlcNAc6ST-1 or I-GlcNAc6ST gene.

2. The method of claim 1, wherein said antigen is present in cells transduced with HEC-GlcNAc6ST gene and is absent in cells transduced with GlcNAc6ST-1 gene or I-GlcNAc6ST gene.

3. The method of claim 1, wherein said antigen comprises the sugar residues expressed by the following formula:

$$R1\text{-Gal}\beta1\text{-}3/4(SO_3\text{-}6)\,\text{GlcNAc}\beta1\text{-}R2$$

where, R1 represents sugar residues added by other enzymes and is not limited in structure; Gal β represents β galactose, GlcNAc β represents β N-acetylglucosamine, Gal β1-3/4 represents binding of 1 position of Gal β and 3 position and/or 4 position of GlcNAc β, (SO$_3$-6) represents addition of a sulfate group to 6 position of GlcNAc β, R2 represents –3GalNAc α, –3Gal β or –2Manα and binds to 1 position of GlcNAc β.

4. The method according to claim 1, wherein said antibody is MECA-79 antibody.

5. A method for examining colorectal cancer and colorectal adenoma comprising:
    a) providing a patient in need of screening for colorectal cancer or adenoma; and
    b) assaying the binding of MECA-79 antibody or another antibody having the same binding specificity with tissues, body fluid, feces, or extract thereof of the patient.

6. The method according to claim 5 comprising binding a labeled probe to said antibody and assaying the label qualitatively or quantitatively.

7. The method of claim 1 wherein the binding of the antibody is performed in feces or extracts thereof.

8. The method of claim 5 wherein the binding of the antibody is performed in feces or extracts thereof.

9. The method of claim 1 wherein the binding of the antibody is performed in body fluid or extracts thereof.

10. The method of claim 5 wherein the binding of the antibody is performed in body fluid or extracts thereof.

* * * * *

UNITED STATES PATENT AND TRADEMARK OFFICE
CERTIFICATE OF CORRECTION

PATENT NO. : 7,601,348 B2  Page 1 of 1
APPLICATION NO. : 10/568544
DATED : October 13, 2009
INVENTOR(S) : Kannagi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 86 days.

Signed and Sealed this

Fifth Day of October, 2010

David J. Kappos
*Director of the United States Patent and Trademark Office*